US011883111B2

(12) United States Patent
Presa Alonso et al.

(10) Patent No.: US 11,883,111 B2
(45) Date of Patent: Jan. 30, 2024

(54) SURGICAL ROBOT FOR ORTHOPAEDIC INTERVENTIONS

(71) Applicant: Cyber Surgery, S.L., San Sebastian (ES)

(72) Inventors: Jorge Presa Alonso, Mendaro (ES); Jon Oñativia Bravo, Mendaro (ES); Álvaro Escudero Martínez De Ibarreta, Mendaro (ES); Alfonso Urzainqui Glaria, Mendaro (ES); Emilio Sanchez Tapia, Mendaro (ES)

(73) Assignee: Cyber Surgery, S.L., San Sebastian (ES)

(*) Notice: Subject to any disclaimer, the term of this patent is extended or adjusted under 35 U.S.C. 154(b) by 875 days.

(21) Appl. No.: 16/612,685

(22) PCT Filed: May 12, 2017

(86) PCT No.: PCT/ES2017/070305
§ 371 (c)(1),
(2) Date: Nov. 11, 2019

(87) PCT Pub. No.: WO2018/206830
PCT Pub. Date: Nov. 15, 2018

(65) Prior Publication Data
US 2020/0229871 A1 Jul. 23, 2020

(51) Int. Cl.
A61B 34/20 (2016.01)
A61B 34/30 (2016.01)
(Continued)

(52) U.S. Cl.
CPC .......... A61B 34/20 (2016.02); A61B 17/1757 (2013.01); A61B 17/7074 (2013.01);
(Continued)

(58) Field of Classification Search
CPC .............................................. A61B 2034/2059
See application file for complete search history.

(56) References Cited

U.S. PATENT DOCUMENTS 5,410,944 A * 5/1995 Cushman ................... B25J 9/14
901/29
6,322,567 B1 * 11/2001 Mittelstadt ............. A61B 34/70
606/130

(Continued)

FOREIGN PATENT DOCUMENTS

RU 2491161 C1 8/2013
WO 2017037127 A1 3/2017

OTHER PUBLICATIONS

International Search Report; PCT/ES2017/070305; dated Feb. 26, 2018; 10 pages.

(Continued)

Primary Examiner — Tessa M Matthews
(74) Attorney, Agent, or Firm — Knobbe, Martens, Olson & Bear, LLP

(57) ABSTRACT

Surgical robot for tracking and compensating bone movement, the robot comprising: a robot arm (3) and a tool guide (5) at the arm's end-effector, a tracker (1) attached to the robot arm at the same plane as the tool guide, the tracker comprising an assembly of articulated segments (1a-1d) and encoders (2) associated to the segments such that movement of the tracker is allowed and monitored in at least six degrees of freedom. The tracker base and the tool guide share the same frame, that is, are on the same plane, so that the system is able to determine directly the exact positioning of the tool guide with respect to the tracked bone without any intermediate device. This way, an optical tracker and the associated cameras can be dispensed with.

8 Claims, 6 Drawing Sheets

(51) Int. Cl.
  *A61B 17/17* (2006.01)
  *A61B 17/70* (2006.01)
  *A61B 17/00* (2006.01)

(52) U.S. Cl.
  CPC .... *A61B 34/30* (2016.02); *A61B 2017/00694* (2013.01); *A61B 2034/2055* (2016.02); *A61B 2034/2059* (2016.02)

(56) References Cited

U.S. PATENT DOCUMENTS

| | | | |
|---|---|---|---|
| 2006/0142657 A1* | 6/2006 | Quaid | A61B 17/1703 600/424 |
| 2009/0306499 A1* | 12/2009 | Van Vorhis | A61B 34/20 606/130 |
| 2013/0096573 A1 | 4/2013 | Kang et al. | |
| 2013/0096574 A1 | 4/2013 | Kang et al. | |
| 2016/0228189 A1 | 8/2016 | Goldenberg et al. | |
| 2016/0346052 A1 | 12/2016 | Rosielle | |
| 2017/0056086 A1 | 3/2017 | Kostrzewski et al. | |
| 2017/0112505 A1 | 4/2017 | Morash | |
| 2018/0168750 A1* | 6/2018 | Staunton | A61B 34/76 |

OTHER PUBLICATIONS

Office Action in India Application No. 201917051331 dated Dec. 23, 2021 in 5 pages.
Office Action dated May 12, 2023 in Chinese Application No. 201780090722.2 and its English machine translation.

\* cited by examiner

SURGICAL ROBOT FOR ORTHOPAEDIC INTERVENTIONS

BACKGROUND OF THE INVENTION

Field of the Invention

The present invention relates to robots for orthopedic interventions, more particularly, to a robot for assisting in the insertion of screws that incorporates means for tracking and compensating for bone movement.

Description of the Related Art

Use of pedicle screw systems for spinal stabilization has become increasingly common in spine surgery. This technology is nowadays used when performing fusion operations in the spine, due to the purported improved fusion rates and rigidity afforded by these constructs. A variety of pedicle screw systems have been described and new techniques are being developed. Traditional techniques depend heavily on the dexterity of the surgeon; techniques that make use of navigation need an external device. Robotic assisted surgery uses a robotic system combined with a tracking device that provides a robust guide to the surgeon.

In U.S. Pat. No. 6,322,567, a system for tracking and compensating for bone movements is described. The system is based on determining a spatial relationship between the surgical robotic arm and bone, and tracking translational and rotational movements of bone with a bone motion detector. The accuracy of this approach is inherently limited by the absolute accuracy of the surgical robotic arm which is responsible for compensating bone motion. Additionally the system relies on a calibration procedure that determines the transformational relationship between the coordinate system of the surgical robotic arm and the coordinate system of the tracking part. Accuracy of the robotic arm and that of the calibration procedure are two intrinsic limitations of this design that introduce non-negligible errors in the system that may have an impact in the device's overall performance. Moreover, the registration procedure depends as well on measuring a set of points in the bone by a human operator that manipulates the tracking system. This last stage introduces errors that can be unpredictable.

SUMMARY OF THE INVENTION

The present invention provides a surgical robot that tracks and compensates for bone movement that comprises a mechanical tracker and a tool guide at the end-effector of a robotic arm. The tracker base and the tool guide share the same reference system, that is, are on the same plane, so that the system is able to determine directly the exact positioning of the tool guide with respect to the tracked bone without any intermediate device. This way, an optical tracker and the associated cameras can be dispensed with, which makes the operating area free of cameras and other devices that hamper the procedures.

The tracker determines the spatial relationship between the robotic arm and the bone by tracking the position of the bone in three perpendicular axes (x,y,z) and the orientation ($\alpha,\beta,\gamma$) with respect to three perpendicular axes, that is, six parameters. Therefore, the tracker is a mechanical system that has to present at least six degrees of freedom in order to track those six parameters. This is achieved by assembly of articulated segments and encoders associated to the segments. In a first embodiment, the tracker is an assembly of four articulated segments with six rotational degrees of freedom. In another embodiment, the tracker is provided with six or seven degrees of freedom where one of the degrees of freedom is a variable length segment and the other ones are rotational degrees of freedom.

BRIEF DESCRIPTION OF THE DRAWINGS

To complete the description and provide for better understanding of the invention, a set of drawings is provided. Said drawings illustrate a preferred embodiment of the invention, which should not be interpreted as restricting the scope of the invention, but just as an example of how the invention can be carried out.

DESCRIPTION OF THE PREFERRED EMBODIMENTS

Figure 1:
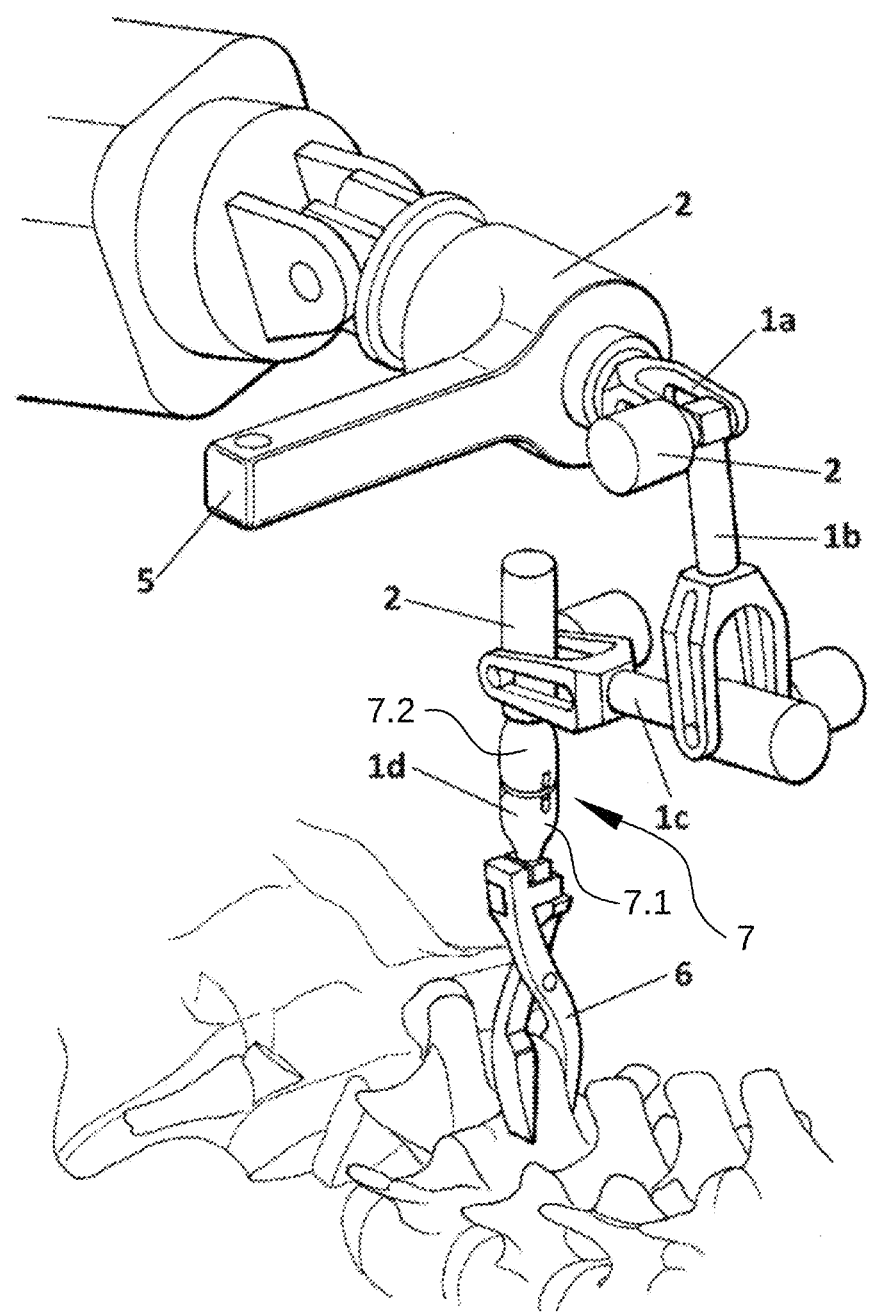
FIG. 1 shows the surgical robot with tracking device of the invention.

With reference to FIG. 1, the surgical robot of the invention is provided with a tracking device. In a first embodiment, the tracker is made of four rigid bodies or segments (1a-1d) linked so that the device is articulated. The tracker presents at least 6 degrees of freedom in order to track the position (x, y, z) and orientation ($\alpha,\beta,\gamma$) in three perpendicular axes of a coordinate system. Each degree of freedom is constantly monitored with a high resolution encoder (2), thus, the position and orientation of the tip of the tracker with respect to its base (3) is known at any given time. The base of the tracker (3) is fixed to the end-effector of the robotic surgical arm. The same end-effector presents a tool guide (5) as well. This tool guide will be placed in space according to the planned locations to allow the surgeon to perform the operation. Both the tracking device and the tool guide share the same base in order to monitor the geometrical relationship between the tool guide and the bone when the tip of the tracking device is attached to the bone. The exact geometrical relationship between the tool guide and the tracker base is established during the manufacturing process and does not need to be calibrated during the lifetime of the system since both elements belong to the same rigid body. During surgery the tip of the tracker is attached to a clamp (6), preferably with a mechanical magnetic coupling mechanism, and the clamp is fixed to the bone. This coupling mechanism has a detector that notifies the system when the tracker is attached to the clamp. If the coupling mechanism is detached unexpectedly, an alarm is triggered and the robotic system goes into a safety mode to guarantee that no harm is produced.

It is important to note that the tracker is a light-weight mechanical device that exerts a negligible force to the bone. Moreover, the magnetic coupling mechanism or kinematic coupler (7) guarantees that the link that is established between the robotic arm and the clamp can be easily released at any time. The force of the magnet is such that when the two parts are coupled, the tip of the tracker and the bone form a rigid body. For these reasons, the segments of the tracker have to be made of a material that provides stiffness without increasing considerably the weight of the overall structure. Moreover, the material has to be paramagnetic in order to avoid the propagation of the magnetic field that is generated by the magnet of the tip of the tracker to the rest of the structure. If this magnetic field is propagated along the segments of the tracker the relative motion between the segments could be affected. Aluminium alloys satisfy such requirements since they present a high strength-to-weight ratio. For instance, aluminium alloy 7075, which is used in a variety of applications such as marine, automotive and aviation, is a good example of material that could be used in the invention. Aluminium alloy 7075 is a very strong material with a strength comparable to many steels and is commonly used in the manufacture of aircraft and other aerospace applications. Titanium is also an appropriate material since it satisfies the previously described properties. For instance, Titanium alloy Ti6Al4V is commonly used in such applications. The relative motion between each segment is restricted by the use of ball bearings or needle roller bearings with radial load direction that allow rotational movement around the desired fixed axes. These fixed axes can be the longitudinal axis or the transverse axis of each joint or a combination of both. Such movements are monitored by rotary encoders that convert angular positions to digital signals.

Figure 3C:
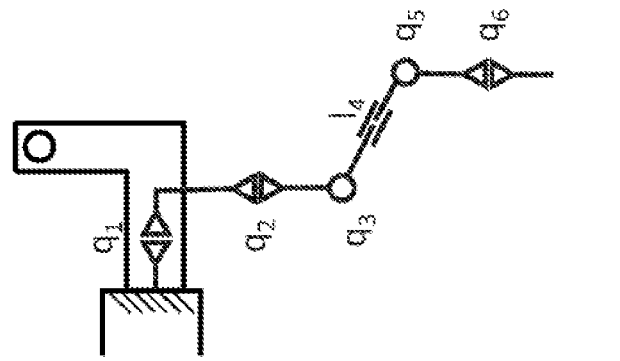
FIGS. 3a-3c show three possible implementations of the invention, two with six and one with seven degrees of freedom.
Figure 3B:
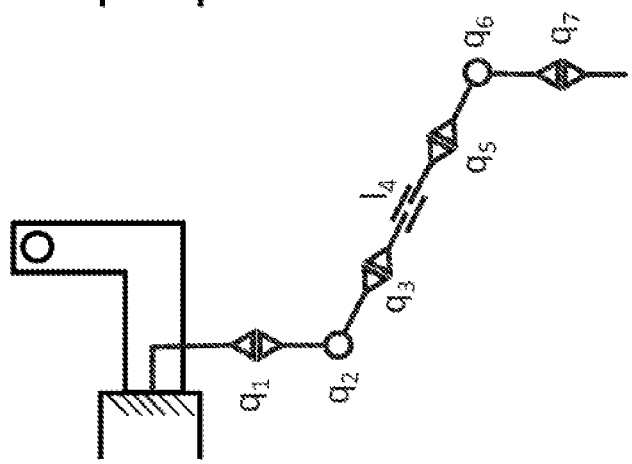
Figure 3A:
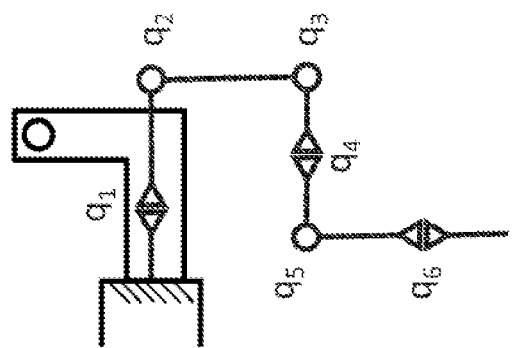

In the first embodiment, the tracker is a kinematic chain (an assembly of articulated segments) with at least six degrees of freedom (FIGS. 1 and 3a). Preferably, the tracker has four articulated segments and six rotary encoders (q1-q6). The first encoder tracks the rotation of the first segment along its longitudinal axis. The second encoder tracks the angle formed by the first and second segment, that is, the rotation along a transverse axis that is perpendicular to the plane that contains the first and second segments. The third encoder tracks the transverse axis between the second and third segments. The fourth encoder tracks the rotation along the longitudinal axis of the third segment. The fifth encoder tracks the transverse angle between the third and fourth segments. And the sixth encoder tracks the rotation along the longitudinal axis of the fourth segment. The rotations and translations along these axes determine the kinematic equations that relate the coordinate system of the base of the tracker and the coordinate system of the tip of the tracker.

In an alternate embodiment shown in FIG. 3b, the tracker may comprise seven degrees of freedom, where for instance six of them are angular and one is longitudinal, that is, a segment of variable length. In such approach, the rotational degrees of freedom are monitored with rotary encoders (q1-q3 and q5-q7) and the longitudinal degree of freedom is monitored with a linear encoder (14). With reference to FIG. 3b, the first encoder tracks the angle formed by the first and second segment. The second encoder tracks the rotation along the longitudinal axis of the second segment. The third encoder tracks the angle formed by the second and third segment. The fourth encoder is a linear encoder that monitors the changes in length of the third segment. The fifth encoder tracks the rotation along the longitudinal axis of the third segment. The sixth encoder tracks the angle formed by the third and fourth segment. And the seventh encoder tracks the rotation along the longitudinal axis of the fourth segment.

In an alternate embodiment shown in FIG. 3c, the tracker may comprise six degrees of freedom, where for instance five of them are angular and one is longitudinal. In such approach, the rotational degrees of freedom are monitored with rotary encoders (q1-q3 and q5-q6) and the longitudinal degree of freedom is monitored with a linear encoder (14). With reference to FIG. 3c, the first encoder tracks the rotation of the first segment along its longitudinal axis. The second encoder tracks the rotation along the longitudinal axis of the second segment. The third encoder tracks the angle formed by the second and third segment. The fourth encoder is a linear encoder that monitors the changes in length of the third segment. The fifth encoder tracks the angle formed by the third and fourth segment. And the six encoder tracks the rotation along the longitudinal axis of the fourth segment.

Alternatively, the tracker can be designed with a different combination of linear and rotary encoders. The minimum requirement is that movement of the mechanical system is allowed in at least six degrees of freedom and that these movements are monitored with encoders.

The exact position and orientation of the tip of the tracker are computed in a processing unit where the signals of the encoders are combined with the kinematic equations of the tracker to output the transformation that relates the base of the tracker with respect to the end of the tracker. The accuracy of the tracker depends on the length of the segments, the resolution of the encoders and the manufacturing and mounting process of the tracker itself. With a combination of four segments of lengths of the order 10 cm and six rotary encoders with resolutions of 16 bits an overall theoretical accuracy of the order of 50 μm can be achieved.

The rotary encoders might be of at least one of the following two types: absolute or incremental. Absolute encoders provide a unique digital code for each distinct angle, as long as the angular variation exceeds the resolution of the encoder. The relationship between the actual reading of the absolute encoder and the physical angle that it measures is established when the system is assembled. Thus, a tracker made of absolute encoders is able to compute the position and orientation of the tip directly when the system is powered on and does not need any calibration position.

Figure 6:
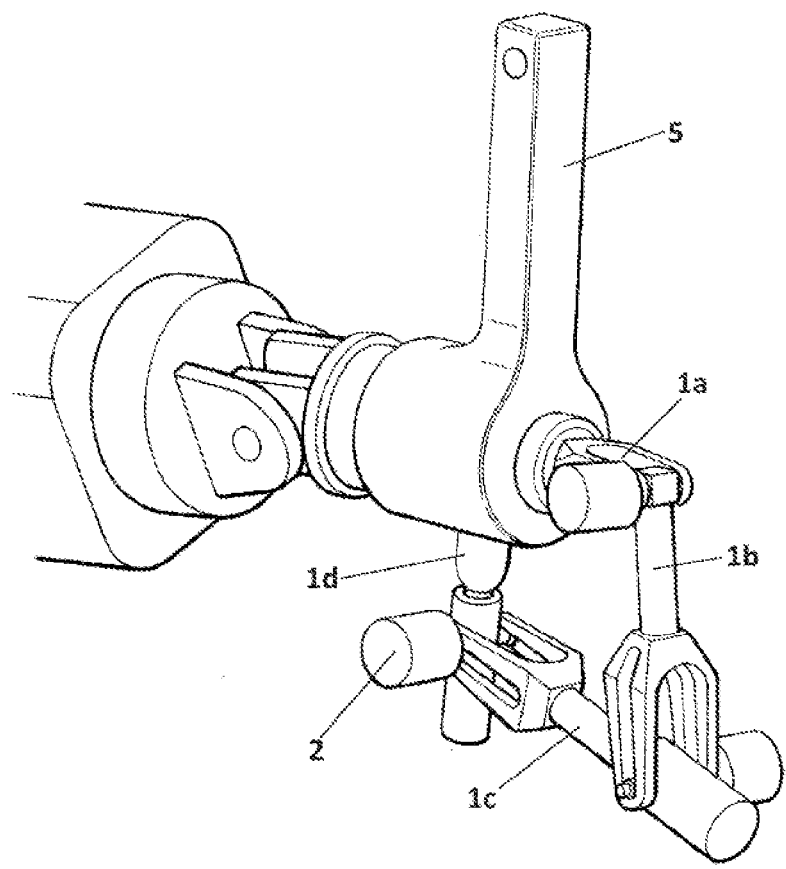
FIG. 6 is a representation of the tracking device in its calibration position.

Incremental encoders measure the angle difference between the angular position when the encoder is powered on (or reset) and its current position. The advantage of this type of encoders is that higher accuracies can be achieved with smaller sizes. However, a known calibration position for each encoder is needed. In the present invention, the tracker provides a unique calibration position with its tip fixed to the base in order to reset the incremental encoders in a known position. This calibration position is illustrated in FIG. 6. Normal usage of a tracker made of incremental encoders starts by resetting the tracker in the calibration position. This calibration position can be used as well as a sanity check at any time during normal usage to verify that the tracker is working properly since the incremental encoders should read a value of zero when they return to the position where they have been reset.

The tool guide has to present a high degree of stiffness since the surgeon will perform the operation through this element. Additionally, the tool guide is directly fixed to the end-effector of the robot and therefore its weight is supported by the robot. This fact relaxes the light-weight constraints that present other elements of the system such as the segments of the tracker. Consequently the material of choice for the tool guide can be stainless steel, which is heavier than aluminium alloys but is also stiffer. The tool guide will be placed in space by the robot according to the planned locations to allow the surgeon to perform the operation. Examples of surgical tools that can be used to perform a pedicle screw insertion through the tool guide are K-wires, pedicle access systems such as awls or reamers, dilators, pedicle probes etc.

The targeted operation is the insertion of pedicle screws in vertebrae, but the invention can also be extended to other types of surgery. The precise location of the screws might be planned before the patient goes into the operating room on a pre-surgical image of the patient or can be planned during the surgery if an intra-operative three dimensional imaging device is available, usually a computerized tomography system (CT). Planning the surgery includes defining the size, location and orientation of pedicle screws in the targeted vertebrae.

In the operating room, the robotically assisted system has to establish first the exact position of the patient. This step, called registration, relates the position and orientation of the real vertebra with respect to the pre-surgical image of the vertebra where the surgery has been planned. The registration process includes fixing a clamp to the targeted area and taking an intra-operative image. At this point, the exact location and orientation of the clamp with respect to the bone is determined. If a pre-surgical plan is available, the plan is transferred to the intra-operative image of the bone. Otherwise, the surgeon plans the exact location of the screws directly in the intra-operative image of the patient.

Note that the clamp is attached to the bone and therefore the clamp and the target share the same coordinate system. Once the tracker tip is coupled with the clamp, the target location defined in the vertebral coordinate system can be transformed to the tracker coordinate system. It is thus possible to monitor the geometrical relationship between the tool guide and the target location. With reference to FIG. 1, the tracker is fixed to the end-effector of the robot and the tip or distal end of the tracker is coupled with the clamp (6), which in turn is attached to the bone. In this situation, the system is able to localize and track in real time the target location in the bone. The robot can therefore be commanded to align the tool guide with the target location and to maintain this geometrical relationship. If movement of the bone occurs, the displacement is detected by the tracker and the robot updates its position in order to preserve the alignment of the tool guide.

Figure 2:
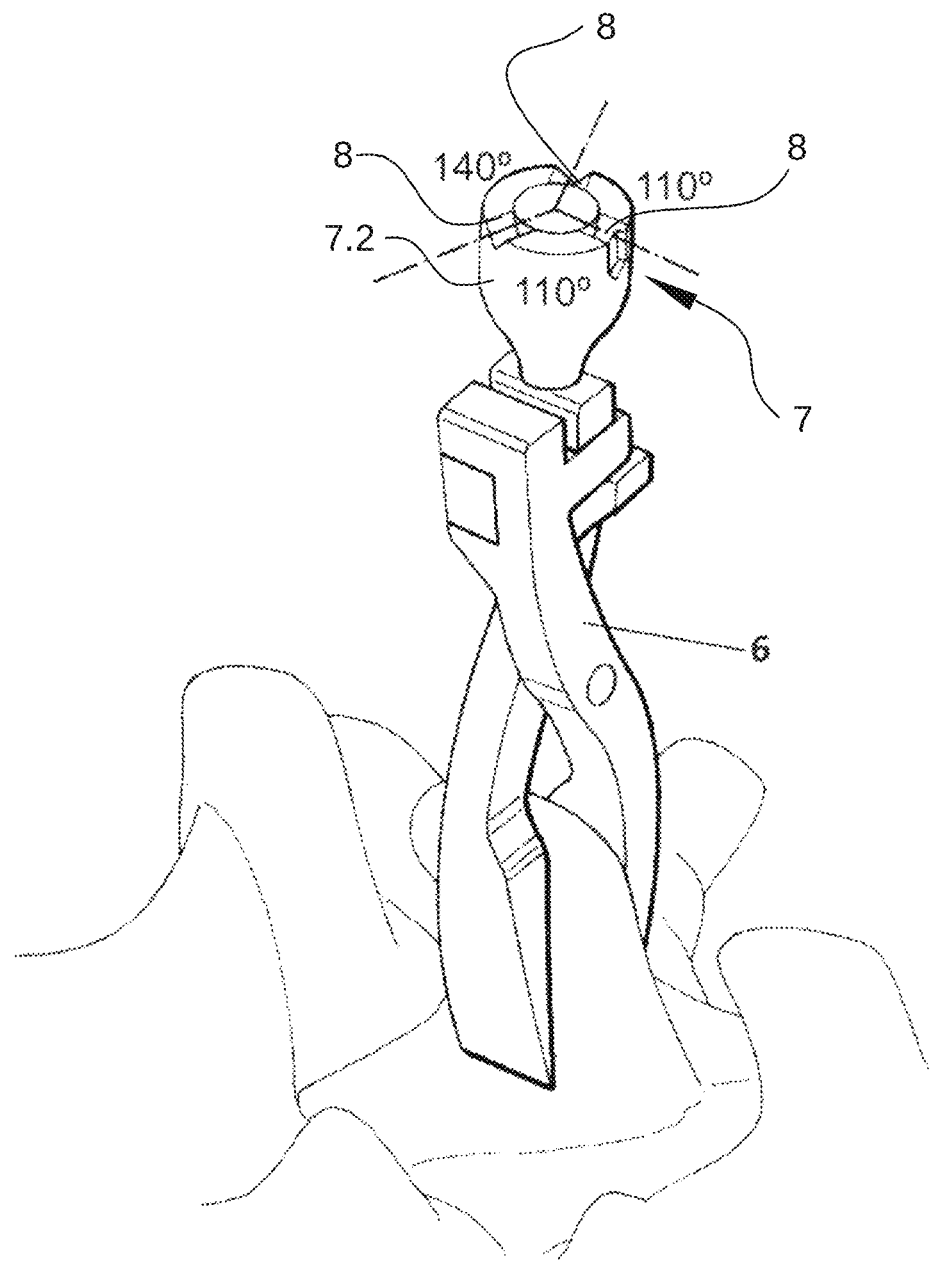
FIG. 2 shows details of the clamp of the system according to the invention.

The coupling mechanism between the tip of the tracker and the clamp is based on a magnetic kinematic coupling system (FIG. 2) which comprises two portions, each portion comprising a magnet, the magnets being of opposite polarities so that they cooperate with each other to form the coupling. A portion, corresponding to a base of the coupling mechanism, is provided at the clamp and the other portion, corresponding to a top portion of the coupling mechanism, is provided at the tracker, attached to the last of the segments at the distal end. Preferably, three V-shaped grooves on the clamp portion and three spheres on the tracker portion provide the mechanical coupling together with the magnets. This coupling creates a precise and repeatable interface between the two rigid bodies. This system provides six contact points—two per sphere—in order to guarantee that the coupling mechanism constrains the six degrees of freedom (three degrees of freedom for the position and another three for the rotation) of the relative movement between the clamp and the tip of the tracker. A magnet in the center of each portion provides the strength required to avoid any relative movement between the clamp and the tip of the tracker. The force exerted by the magnet is such that it ensures the connection between the clamp and the tracker while the robot is moving. However, this force is such that the connection can be released by a human operator in order to allow the system to be easily removed at any time. The most stable kinematic coupling would be obtained when the three V-shaped grooves form angles of 120°. However, for the invention it is preferred that the three V-shaped grooves form three angles such that the coupling mechanism can only be engaged in a unique position. For instance, angles of 110°, 110° and 140° guarantee that the coupling mechanism is engaged in a unique position. For this purpose, at least one of the angles must be different from the other two.

Figure 4:
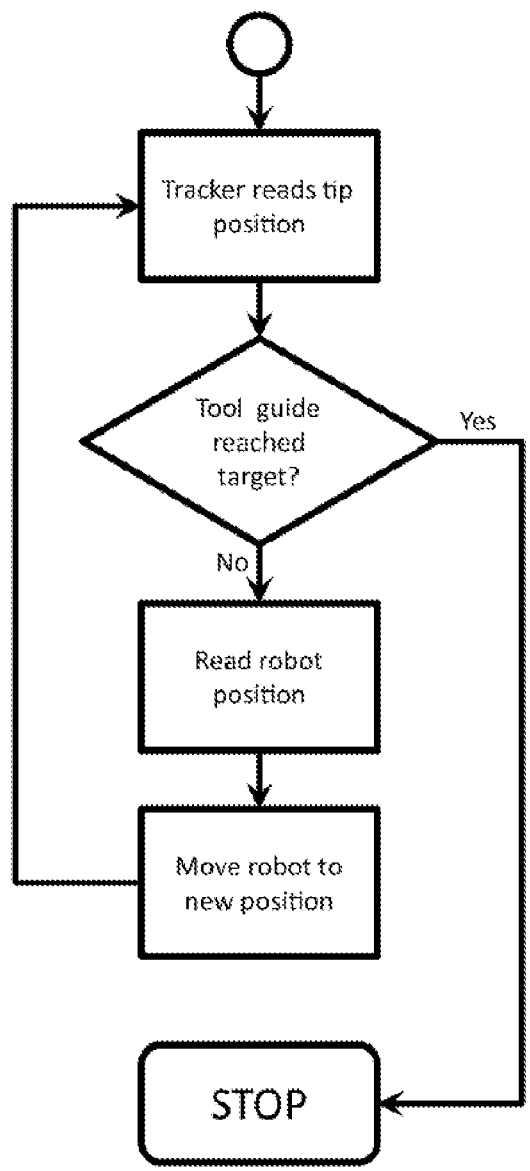
FIGS. 4 and 5 are flowcharts which describe the working principle of the invention.
Figure 5:
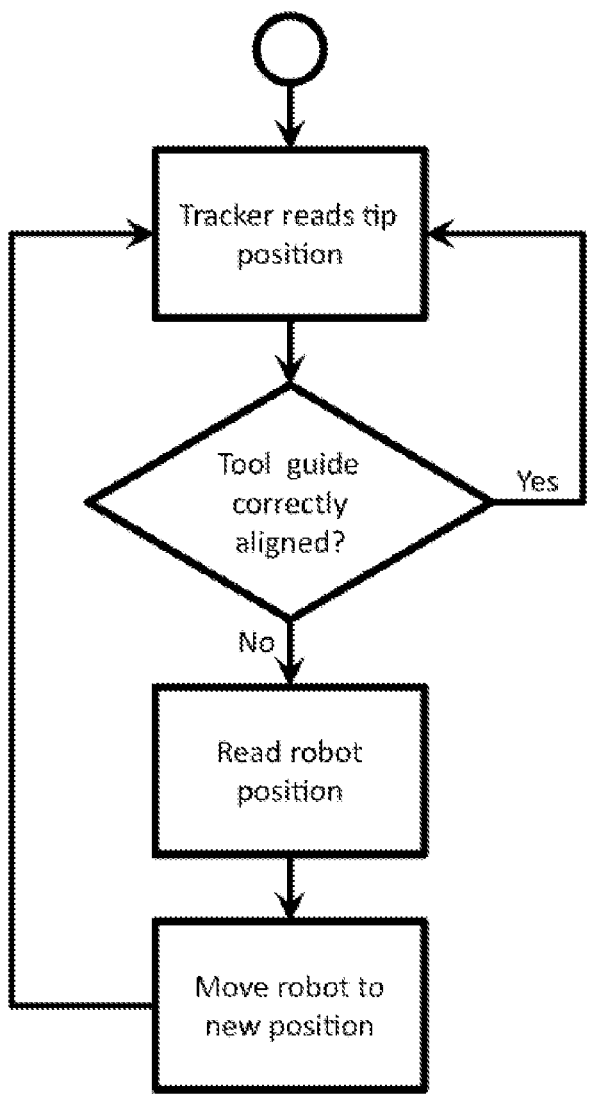

When the tracking device is coupled to the clamp, the robot can operate in various modes. It can be commanded to go to a planned position, where the planned position is expressed in the coordinate system of the tracking clamp. This operation is illustrated in the flowchart of FIG. 4. In a stationary situation where the bone has no movement, the robot will stop when the tool guide reaches the desired position. In a different mode, the tool guide is already aligned with the target location and the robot updates its position in order to keep this alignment by compensating for bone movement. This second functioning mode is illustrated in the flowchart of FIG. 5. Note that in this mode the robot never stops since it is constantly updating its position to keep the alignment of the tool guide and the target location.

The clamp and the tracker can present a detection mechanism that notifies the system when the tracker is attached to the clamp. This detection mechanism comprises an electric circuit connected to a processing unit that is able to identify when a connection has been established. The base portion (7.1) of the coupling mechanism or kinematic coupler (7) is provided with a passive electric circuit and the top portion (7.2) connects the base portion to a processing unit. The processing unit applies a small voltage, therefore, when the connection is established the electric circuit is closed and a current is detected. For this purpose, the spheres of the kinematic coupling mechanism are made of an electrically conductive material and are electrically connected to the processing unit. The V-shaped grooves (8) present an electrically conductive section where the spheres make contact in order to establish the electrical connection between the top and base portion.

As it is used herein, the term "comprises" and derivations thereof (such as "comprising", etc.) should not be understood in an excluding sense, that is, these terms should not be interpreted as excluding the possibility that what is described and defined may include further elements, steps, etc.

On the other hand, the invention is obviously not limited to the specific embodiment(s) described herein, but also encompasses any variations that may be considered by any person skilled in the art (for example, as regards the choice of materials, dimensions, components, configuration, etc.) to be within the general scope of the invention as defined in the claims.

The invention claimed is:

1. A surgical robot for tracking and compensating bone movement, the robot comprising:
    a robot arm comprising an end-effector;
    a tool guide located at the end-effector of the robot arm; and
    a tracker configured to determine a spatial relationship between the robot arm and a bone, the tracker comprising:
        a base fixed to the end-effector of the robot arm,
        a distal end adapted to be coupled with a clamp,
        an assembly of articulated segments configuring a kinematic chain that connects the base with the distal end, and encoders associated to the articulated segments and configured to track movement of the articulated segments, wherein a movement of the tracker is allowed and monitored in at least six degrees of freedom, the tracker and the tool guide share the same base in order to monitor a geometrical relationship between the tool guide and the bone when the distal end of the tracker is attached to the bone, the surgical robot further comprises a clamp, wherein the clamp is removably attached with a kinematic coupler to an articulated segment of the distal end of the tracker configured to be closer to a patient, and the kinematic coupler comprises:

a base portion located at the clamp and comprising a first magnet, and a top portion located at the tracker and fixed to the last articulated segment of the tracker at the distal end, the top portion comprising a second magnet of opposite polarity to the first magnet.

2. The surgical robot according to claim 1, wherein the tracker comprises four articulated segments and six associated rotary encoders.

3. The surgical robot according to claim 1, wherein the tracker comprises four articulated segments and five associated rotary encoders, and one of the segments is configured to change its length and includes an associated linear encoder such that the movement of the tracker is allowed and monitored in six degrees of freedom.

4. The surgical robot according to claim 1, wherein the tracker includes four articulated segments and six associated rotary encoders, and one of the segments is configured to change its length and includes an associated linear encoder such that the movement of the tracker is allowed and monitored in seven degrees of freedom.

5. The surgical robot according to claim 1, wherein the articulated segments are made of light paramagnetic material.

6. The surgical robot according to claim 1, wherein the top portion comprises three spheres, the base portion comprising three V-shaped grooves, the grooves forming three angles, and wherein at least one of the angles is different from the other two, such that the spheres and the grooves are configured to cooperate with each other to form the coupling.

7. The surgical robot according to claim 6, wherein the spheres of the top portion of the kinematic coupler comprises electrically conductive material and are electrically connected to a processor and the V-shaped grooves present an electrically conductive section.

8. The surgical robot according to claim 1, wherein the articulated segments of the tracker comprise an aluminium alloy or a titanium alloy.

* * * * *